(12) United States Patent
Blocher

(10) Patent No.: US 7,611,511 B2
(45) Date of Patent: Nov. 3, 2009

(54) BIPOLAR MEDICAL INSTRUMENT AND ELECTROSURGICAL SYSTEM COMPRISING SUCH AN INSTRUMENT

(75) Inventor: Martin Blocher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 493 days.

(21) Appl. No.: 11/146,262

(22) Filed: Jun. 6, 2005

(65) Prior Publication Data

US 2005/0267469 A1 Dec. 1, 2005

Related U.S. Application Data

(63) Continuation of application No. PCT/EP03/13736, filed on Dec. 4, 2003.

(30) Foreign Application Priority Data

Dec. 6, 2002 (DE) .............................. 102 58 730

(51) Int. Cl.
*A61B 18/14* (2006.01)
(52) U.S. Cl. .......................................... 606/46; 606/48
(58) Field of Classification Search ................... 606/34, 606/48, 50, 46
See application file for complete search history.

(56) References Cited

U.S. PATENT DOCUMENTS

| | | | | |
|---|---|---|---|---|
| 2,056,377 A | | 10/1936 | Wappler | ................ 128/303.14 |
| 4,116,198 A | * | 9/1978 | Roos | ........................... 606/46 |
| 5,419,767 A | | 5/1995 | Eggers et al. | ................ 604/114 |
| 6,142,992 A | * | 11/2000 | Cheng et al. | ................... 606/34 |
| 6,471,701 B2 | * | 10/2002 | Brommersma et al. | ........ 606/46 |
| 6,616,656 B2 | * | 9/2003 | Brommersma | ............... 606/41 |

FOREIGN PATENT DOCUMENTS

| | | |
|---|---|---|
| DE | 2521719 | 6/1985 |
| DE | 3815835 | 11/1989 |
| DE | 4425015 | 1/1996 |
| DE | 100 28 850 | 10/2001 |
| DE | 102 58 730 | 7/2004 |
| EP | 1 163 886 | 6/2001 |
| WO | 99/16371 | 4/1999 |

OTHER PUBLICATIONS

International Search Report (Mar. 31, 2004).

* cited by examiner

*Primary Examiner*—Lee S Cohen
(74) *Attorney, Agent, or Firm*—St. Onge Steward Johnston & Reens LLC

(57) ABSTRACT

A bipolar medical instrument for cutting tissue under the action of high-frequency current comprises an elongate electrode carrier, an active electrode arranged at the distal end of the electrode carrier, and a neutral electrode adjacent to the active electrode, said neutral electrode being arranged entirely to the distal side of said active electrode. The neutral electrode and the active electrode are spaced apart from one another in the direction transverse to the longitudinal direction of the electrode carrier. The invention also describes an electrosurgical system comprising a high-frequency generator and provided with such an instrument.

30 Claims, 3 Drawing Sheets

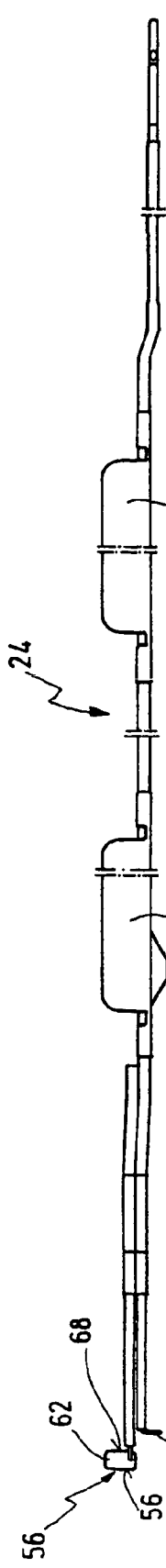
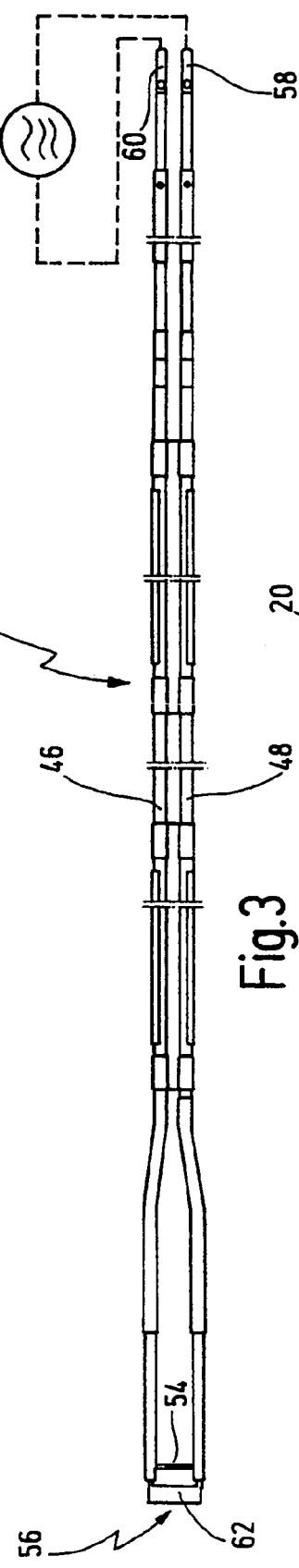
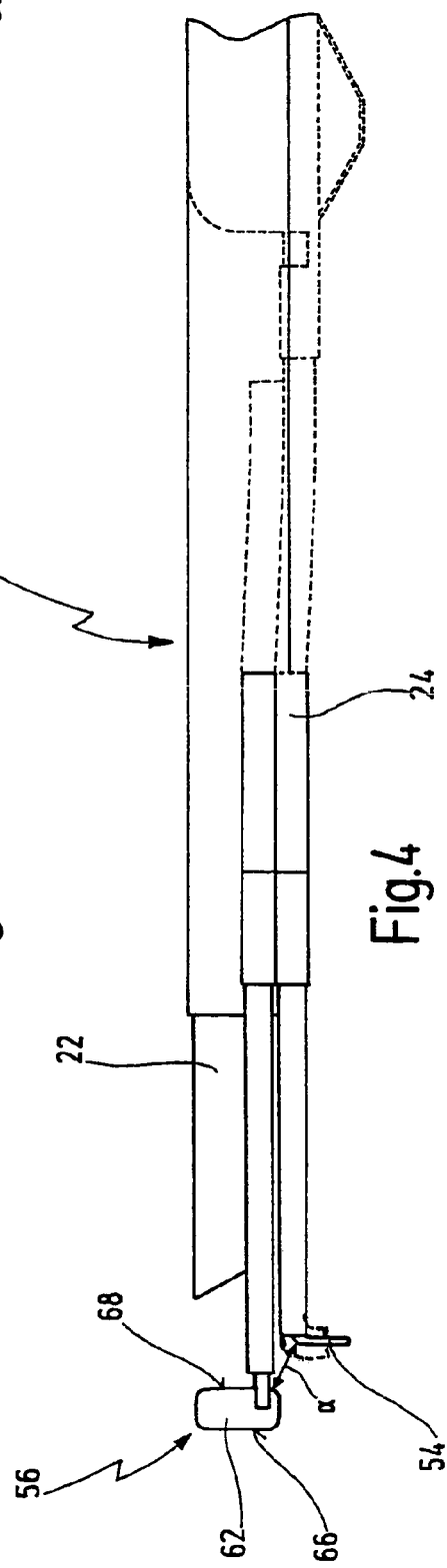

BIPOLAR MEDICAL INSTRUMENT AND ELECTROSURGICAL SYSTEM COMPRISING SUCH AN INSTRUMENT

CROSSED REFERENCE TO RELATED APPLICATIONS

The present application is a continuation of pending international patent application PCT/EP2003/013736 filed on Dec. 4, 2003 which designates the United States, and which claims priority of German patent application no. 102 58 730.2 filed on Dec. 6, 2002.

BACKGROUND OF THE INVENTION

The invention relates to a bipolar medical instrument for cutting tissue under the action of high-frequency current.

The invention further relates to an electrosurgical system, comprising a high-frequency generator and an instrument of the type indicated above.

An instrument and a system of the type mentioned at the outset are used in open surgery, but preferably in minimally invasive surgery, for cutting tissue in the human or animal body.

In the context of the present invention, the instrument mentioned at the outset, when used in minimally invasive surgery, can be combined with an endoscope to form what is known as a resectoscope, or it can itself constitute such a resectoscope.

Electrosurgery, or high-frequency surgery, is employed therapeutically in various medical specialties, for example in urology, gynecology, neurosurgery, abdominal surgery, etc. In urology in particular, prostate tissue is removed endoscopically in minimally invasive surgery by means of an instrument of the type mentioned at the outset.

In electrosurgical resectoscopy, a distinction is made between monopolar and bipolar application of high-frequency current.

In monopolar application, only the active electrode is introduced into the treatment region, while the neutral electrode is arranged externally on the patient. Consequently, the current flow between the active electrode and the neutral electrode passes through the patient's body, the disadvantage being that the current path through the patient cannot be safely controlled, the result of which is the possibility of damage to the organs. In addition, the neutral electrode placed on the patient's body may cause burning of the patient's skin.

In the bipolar technique, on which the present invention is based, the active electrode and the neutral electrode are both introduced into the treatment region. The current flow can in this way be limited in a controllable manner to the area between the active electrode and the neutral electrode. Accordingly, medical instruments of the type mentioned at the outset have been created in which the active electrode and the neutral electrode are arranged on an electrode carrier, in such a way that the active electrode and the neutral electrode can be introduced adjacent to one another into the treatment region.

In bipolar medical instruments of the type mentioned at the outset, the active electrode is usually configured with a small active surface area so that a high current density is created on the active electrode, whereas the neutral electrode is usually configured with a relatively large surface area so that only moderate to low current densities are created on the neutral electrode. The active electrode is accordingly used for cutting, while the neutral electrode is intended as far as possible to have no effect on the tissue and is intended simply to limit the current path to the area between the active electrode and the neutral electrode.

In the instrument known from the document DE-OS 25 21 719, the neutral electrode is configured as a tape loop, while the active electrode is configured as a wire loop. The neutral electrode is located entirely to the distal side of the active electrode and runs parallel to the latter. In this known instrument, it can happen that, when the instrument is placed on the tissue to be treated, the neutral electrode first touches the tissue, before the active electrode contacts the tissue, the result being that, when high-frequency current passes through the electrodes, the tissue in contact with the neutral electrode may possibly be cauterized, or at least damaged, even though this tissue was not to be treated. However, even upon simultaneous contact of active electrode and neutral electrode, tissue which is in contact with the neutral electrode, and which is not intended to be subjected to the effect of the high-frequency current, may be damaged.

In a further illustrative embodiment in the document DE-OS 25 21 719, the neutral electrode, on its side directed away from the active electrode, is covered by a plastic extension which is connected securely to the shaft of the resectoscope, with the result that the abovementioned problem of uninvolved tissue coming into contact with the neutral electrode is avoided. A disadvantage of this, however, is that the neutral electrode is not movable relative to the shaft of the resectoscope. In resectoscopes, however, it may be expedient to move the neutral electrode together with the active electrode relative to the shaft of the resectoscope in order to perform the cutting procedure, whereas the endoscope optical unit should be moved as little as possible, during the cutting procedure, so as not to alter the viewing angle or field of view during cutting, and thus achieve the greatest possible precision in the visual monitoring of the cutting procedure. In addition, in this illustrative embodiment, the neutral electrode is arranged to the proximal side of the active electrode, or it extends both to the proximal side and to the distal side of the active electrode.

Moreover, EP 1 163 886 A2 discloses a resectoscope instrument in which the active electrode and the neutral electrode are electrically separated on their mutually facing sides by an insulating body, such that each straight line of connection between the electrodes passes through the insulating body. This is intended to ensure that the direct current flow between the two electrodes is made difficult or is reduced, as a result of which a greater proportion of the power fed into the instrument will pass from the active electrode into the body tissue and there deploy a cutting action. In this instrument, the insulating body is arranged on the inner face of the neutral electrode directed towards the active electrode and, when the neutral electrode changes position, said insulating body can accordingly move along with it.

None of the known instruments has as yet proven satisfactory in terms of its cutting action.

SUMMARY OF THE INVENTION

The object of the invention is to make available an instrument and a system of the type mentioned at the outset, with which it is possible for tissue to be cut satisfactorily by means of high-frequency current.

According to an aspect of the present invention, a bipolar medical instrument for cutting tissue under the action of high-frequency current is provided, comprising an elongate electrode carrier extending in a longitudinal direction and having a distal end, an active electrode arranged at said distal end of said electrode carrier, a neutral electrode arranged at said distal end of said electrode carrier adjacent to said active electrode and arranged entirely to the distal side of said active electrode so as to be spaced apart from said active electrode in said longitudinal direction, said neutral electrode and said active electrode being also spaced apart from one another in a direction transverse to said longitudinal direction, without having a spatial overlap region in said longitudinal direction and said direction transverse to said longitudinal direction.

An electrosurgical system according to the invention, of the type mentioned at the outset, thus comprises a medical instrument of the abovementioned type.

Tests have shown that the bipolar medical instrument according to the invention provides very good cutting results. The cutting results are excellent, in particular, if the instrument is used in a treatment region in which an electrically conductive liquid is located, for example if, during resection, irrigation is performed with an irrigation liquid rich in electrolytes, for example an isotonic irrigation liquid. The fact that the neutral electrode is positioned to the distal side of the active electrode and is spaced apart there from in the direction transverse to the longitudinal direction of the electrode carrier, and is accordingly located behind and above the active electrode, as seen in the pulling direction of the latter, during the cutting of the tissue, has surprisingly been found to be very effective in terms of the cutting of the tissue.

A further advantage of the medical instrument according to the invention can be seen to lie in the fact that by arranging the neutral electrode to the distal side of the active electrode, and in a position offset in relation to the active electrode in the direction transverse to the longitudinal direction of the electrode carrier, the view of the active electrode is not concealed while working with the instrument, especially when the instrument is used together with an endoscope optical unit. A further advantage is that, while cutting tissue with the active electrode, during which the active electrode and thus the neutral electrode are pulled back in the proximal direction, the neutral electrode does not come into contact with the shaft of the instrument, so that no additional insulating measures are needed for the shaft, and, instead, the shaft can be configured exactly as in a monopolar instrument.

Because it is spaced apart from the active electrode in the direction transverse to the longitudinal direction of the electrode carrier, the neutral electrode does not come into contact with the tissue to be cut when the active electrode is placed on said tissue.

In a preferred embodiment of the instrument, the active electrode is configured as a wire loop, and, alternatively or cumulatively, the neutral electrode is configured as a tape loop, preferably with a curvature oriented away from the active electrode.

With this configuration of the instrument according to the invention, particularly good cutting effects of the instrument according to the invention have been obtained in tests.

In a further preferred embodiment, on the electrode carrier and/or on the neutral electrode, at least one element is present which prevents electrically conductive contact between tissue and an outer face of the neutral electrode directed away from the active electrode, and which, when the neutral electrode changes position, moves along with said neutral electrode.

The at least one element acts in the manner of a spacer between the neutral electrode and uninvolved tissue, and, as a result of this, damage to uninvolved tissue during handling of the instrument in the treatment area is avoided, which is of advantage especially when using the instrument in confined treatment areas because the physician operating the instrument does not have to pay constant attention to keeping the neutral electrode away from uninvolved tissue.

In a further preferred embodiment, the at least one element is itself electrically insulating.

An advantage of this is that electrically conductive contact between the neutral electrode and tissue can be reliably avoided without complicated structural measures, and that the element can be secured directly on the neutral electrode.

In a further preferred embodiment, the at least one element is made from a ceramic material or from a plastic.

This measure has the advantage that the abovementioned materials are inexpensive. As plastics, it is possible to use, for example, materials sold under the trademark Safecoat 720, or, for example, polytetrafluoroethylene. As ceramic material, it is possible to use zirconium oxide, for example.

In a further preferred embodiment, the at least one element is formed by a coating of the neutral electrode.

An advantage of this is that the element preventing contact between the neutral electrode and uninvolved tissue can be applied relatively thinly on the neutral electrode. A suitable coating material is, in particular, polyetheretherketone (PEEK), which has the advantage of being able to withstand high temperatures and of being mechanically strong, in particular resistant to impacts. In this way, the neutral electrode is protected from damage when being autoclaved and when the instrument is in use.

In a further preferred embodiment, the at least one element is secured directly on the outer face of the neutral electrode directed away from the active electrode.

An advantage of this is that the at least one element acting as spacer does not substantially increase the transverse dimension of the electrode arrangement, with the result that the instrument is also especially suitable for minimally invasive surgery, in which miniaturized instruments are required.

In a further preferred embodiment, the at least one element completely covers the outer Face of the neutral electrode.

An advantage of this is that the at least one element can be applied with a very small thickness on the outer face of the neutral electrode, with the result that an electrically conductive contact between the neutral electrode and tissue does not have to be avoided by keeping these spatially distant from one another.

In a further preferred embodiment, the at least one element prevents electrically conductive contact between the distal and/or proximal end face of the neutral electrode and tissue.

An advantage of this is that contact between the neutral electrode and tissue can be reliably avoided even when the electrode carrier and thus the active electrode and neutral electrode are being moved to and fro.

In this connection, it is also preferred if the at least one element is secured directly on the outer face of the neutral electrode directed away from the active electrode and covers the complete area of the distal and/or proximal end face of the neutral electrode.

In a further preferred embodiment of the electrosurgical system, the high-frequency generator is able to output power of at least 200 watt.

It is precisely the combination of the instrument according to the invention and a high-frequency generator of this kind that has in practice proven particularly effective, this being due to the fact that, because the neutral electrode is spaced apart from the active electrode, first only the active electrode comes into contact with the tissue to be cut, while the rear neutral electrode, as viewed In the direction of pulling, Is still located inside the irrigation liquid, and the current for the most part flows only through the isotonic saline solution, and not through the tissue. With higher output of the high-frequency current, however, this problem can be overcome, as has been shown in practice.

It is particularly preferable if the high-frequency generator has an output regulator which is such that the power output by the high-frequency generator before and during penetration of the active electrode into tissue (initial cutting) is greater than during the continued cutting when the active electrode has penetrated into the tissue.

As has been explained above, the initial cutting behavior of the instrument can be decisively improved if the cutting power is increased to values of over 200 watt. However, if this high power output of the high-frequency generator were to be maintained throughout the cutting procedure, this would lead, at least in the initial phase of cutting, to visible carbonization of the tissue, which is undesirable. This disadvantage can be avoided by accordingly reducing the power output of the high-frequency generator during the further cutting.

Further advantages and features will become evident from the following description and from the attached drawing.

It will be appreciated that the features mentioned above and the features still to be explained below can be used not only in the respectively cited combination, but also in other combinations and singly, without departing from the scope of the present invention.

BRIEF DESCRIPTION OF THE DRAWINGS

An illustrative embodiment of the invention is depicted in the drawing and is described in more detail below with reference to this drawing, in which:

FIG. 2 shows an electrode arrangement of the medical instrument in FIG. 1, in a side view and on a larger scale than in FIG. 1;

FIG. 3 shows the electrode arrangement in FIG. 2 in a plan view;

FIG. 4 shows a distal area of the instrument in FIG. 1, in a side view and on a still larger scale;

DETAILED DESCRIPTION OF PREFERRED EMBODIMENTS

Figure 1:
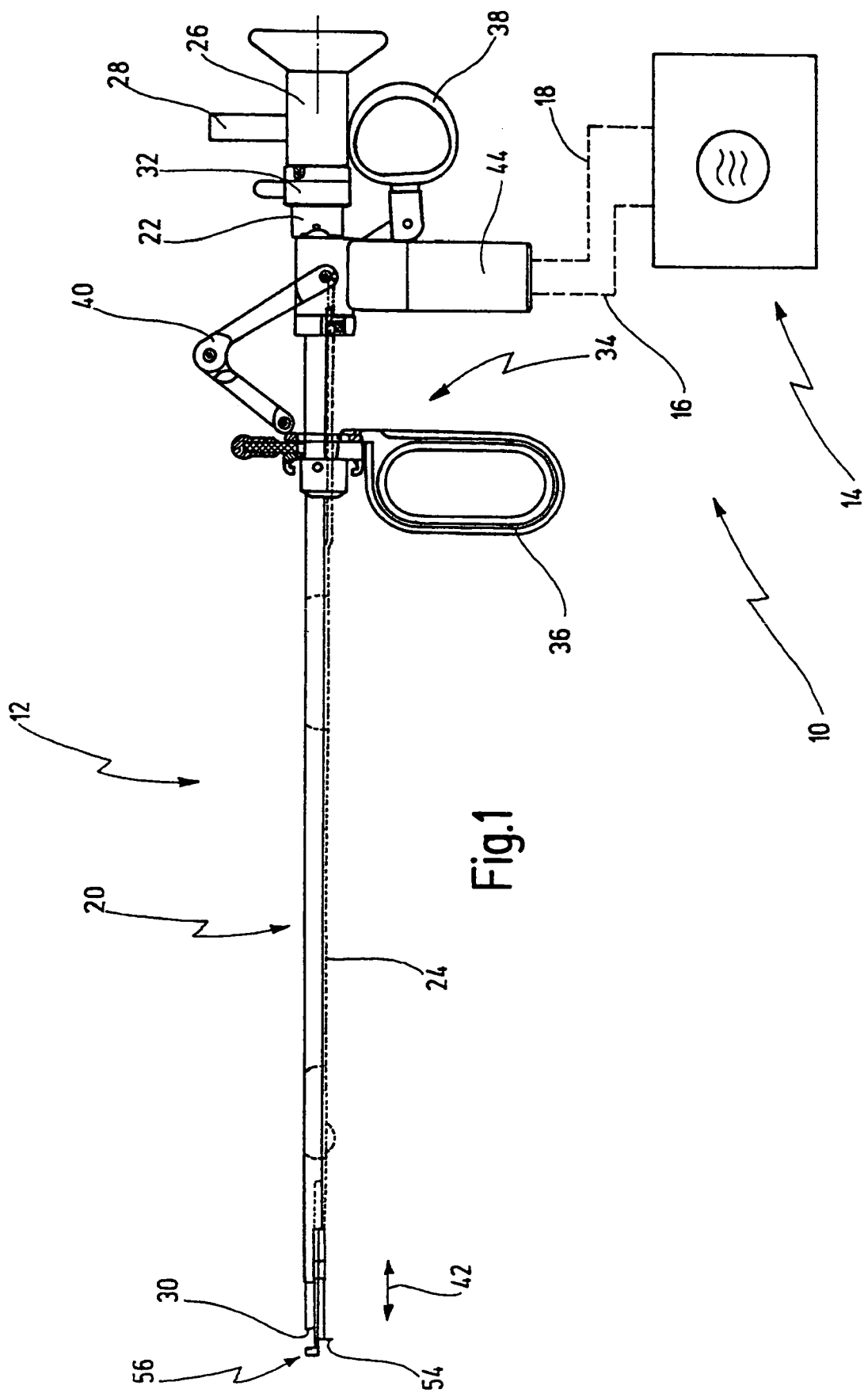
FIG. 1 shows an electrosurgical system with a bipolar medical instrument and, represented extremely schematically, a high-frequency generator, the instrument being seen in a side view.

In FIG. 1, general reference number 10 designates an electrosurgical system which is used in the context of minimally invasive resectoscopy.

The system 10 comprises a bipolar medical instrument 12 in the form of a resectoscope, of which further details are shown in FIGS. 2 to 5.

The system 10 further comprises a high-frequency generator 14, which is shown extremely schematically in FIG. 1. The high-frequency generator 14 generates high-frequency current or high-frequency voltage which is delivered to the instrument 12 via lines 16 and 18, one of which is connected to the active pole of the high-frequency generator 14, and the other of which is connected to the inactive pole of the high-frequency generator 14.

The instrument 12 will first be described in more detail below.

The instrument 12 is used for cutting tissue in the human or animal body under the action of high-frequency current.

The instrument 12 has an elongate shaft 20 in which an endoscope optical unit 22 and an electrode carrier 24 are arranged.

At its proximal end, the endoscope optical unit 22 has an eyepiece 26 and a connector 28 for attachment of a light guide cable for delivering illumination light to the endoscope optical unit 22. The endoscope optical unit 22 extends distally as far as a light exit end 30 which is provided with an oblique viewing lens.

The endoscope optical unit 22 is connected via a coupling 32 to the shaft 20 of the instrument 12 and can be removed from the instrument 12 by releasing the coupling 32.

Moreover, in the proximal area, the instrument 12 has a handle 34 with a finger grip part 36 and a thumb grip part 38, the thumb grip part 38 being movable relative to the finger grip part 36 via a hinge 40. The finger grip part 36 and the thumb grip part 38 can be moved toward and away from one another. By suitable actuation of the handle 34, the electrode carrier 24 can be moved in the longitudinal direction of the shaft 20 relative to the shaft and relative to the endoscope optical unit 22 in the directions of a double arrow.

Finally, the proximal area of the instrument 12 is provided with a plug connector 44 via which the instrument 12 can be connected to the high-frequency generator 14.

Figure 5:
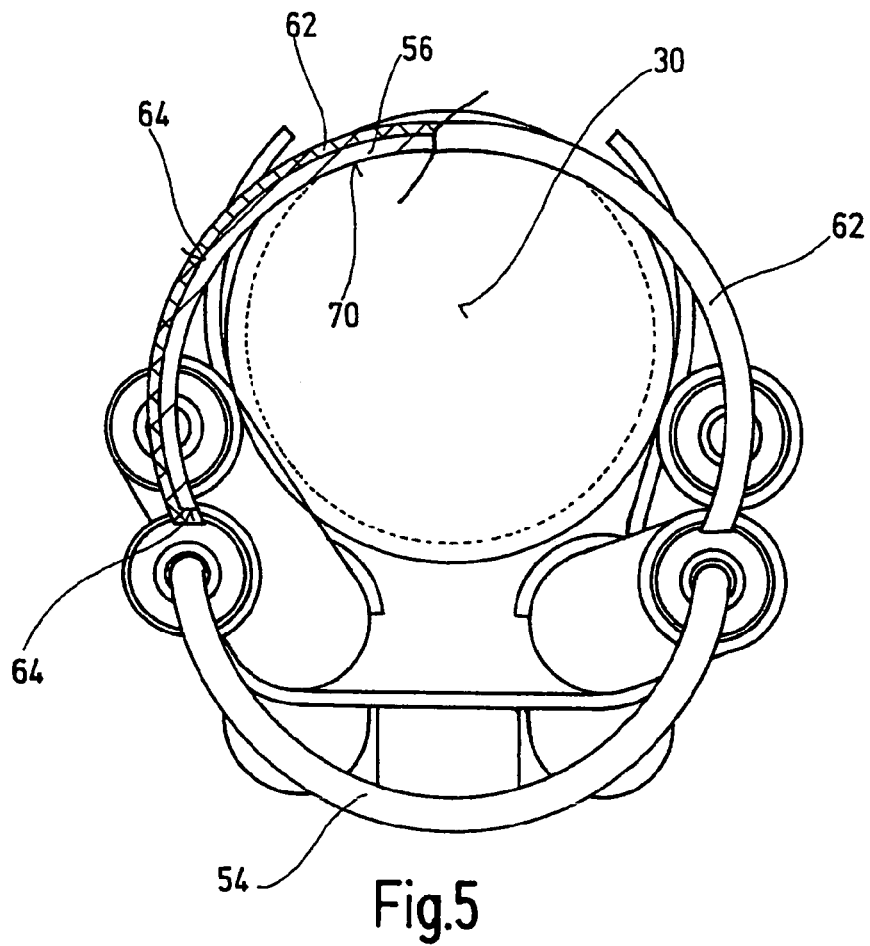
FIG. 5 shows a front view of the instrument in FIG. 1, on a very much enlarged scale.

Further details of the electrode arrangement of the instrument 12 are now described with reference to FIGS. 2 to 5. FIGS. 2 and 3 show the electrode carrier 24 in isolation, while FIG. 4 shows the distal area of the shaft 20 on a still larger scale. FIG. 5 shows a front view of the distal end of the instrument 12.

The electrode carrier 24 is made up of two bars 46 and 48 which extend parallel to one another and run approximately the length of the shaft 20 of the instrument 12. In the central area of the bars 46 and 48, the latter are connected to one another by fixation elements 50 and 52 which have an approximately U-shaped cross section and which also ensure guiding of the electrode carrier 24 along the endoscope optical unit 22 when the electrode carrier 24, as has been described above, is moved relative to the endoscope optical unit.

At the distal end, the electrode carrier 24 has an active electrode 54 and a neutral electrode 56 which is adjacent to the active electrode 54 and which, in FIG. 5, can be seen through partial cutting-away of the drawing.

The neutral electrode 56 is arranged entirely to the distal side of the active electrode 54, i.e. is spaced apart axially from the active electrode 54 as seen in the longitudinal direction of the electrode carrier 24 and represents the outermost distal end of the electrode carrier 24.

The active electrode 54 is configured as a wire loop (cf. FIG. 5) which extends substantially perpendicular to the longitudinal direction of the electrode carrier 24. The neutral electrode 56 is configured as a tape loop, as will be seen by comparing FIGS. 2 to 4 and FIG. 5, which also extends substantially perpendicular to the longitudinal direction of the electrode carrier 24, but whose curvature or concave side is oriented away from the active electrode 54. As can be seen from the figures, the neutral electrode 56 and the active electrode 54 are spaced apart from one another in the direction transverse to the longitudinal direction of the electrode carrier 24. The neutral electrode 56 and the active electrode 54 have no spatial overlap area either in the longitudinal direction of the electrode carrier 24 or in the direction transverse to the longitudinal direction of the electrode carrier 24.

In FIG. 4, the letter d designates a minimum distance between the active electrode 54 and the neutral electrode 56, this distance preferably being in the range of 0.5 to 5 mm, preferably 2.5 mm. The offset between the neutral electrode 56 and the active electrode 54 in the direction transverse to the longitudinal direction of the electrode carrier 24 is preferably in the range of between approximately 0.5 and approximately 3 mm. The axial extent of the neutral electrode 56, i.e. the extent of the neutral electrode 56 in the longitudinal direction of the electrode carrier 24, is preferably in the range of between approximately 1 and approximately 3 mm.

The active electrode 54 is connected conductively via one of the bars, for example bar 48, to a plug contact 58 arranged at the proximal end of the bar 48, while the neutral electrode 56 is then connected conductively to the corresponding plug contact 60 at the proximal end of the bar 46. The bars 46 and 48 are electrically insulated from outside. The active electrode 54 can thus be connected to the active pole of the high-frequency generator 14, while the neutral electrode 56 is connected to the inactive pole of the high-frequency generator 14.

While the active electrode 54 lies free on all sides, i.e. is free of insulation on all sides, an element 62 is provided on the neutral electrode 56 and prevents electrically conductive contact between an outer face 64 (cf. FIG. 5) of the neutral electrode 56 and tissue. For example, the element 62 is secured directly on the neutral electrode 56 so that, when the neutral electrode 56 changes position, for example if the handle 34 is actuated, it moves along with the neutral electrode 56. Alternatively, however, the element 62 can also be connected to the electrode carrier 24 and simply cover the neutral electrode 56.

The element 62 is electrically insulating and is made, for example, from a ceramic material or from plastic. It is particularly preferable if the element 62 is applied in the form of a coating of the neutral electrode 56 with polyetheretherketone (PEEK). The element 62 covers the entire outer face 64 of the neutral electrode 56, and specifically also at a distal end face 66 and a proximal end face 68 of the neutral electrode 56. The element 62 prevents the outside of the neutral electrode 56 from coming into contact with uninvolved tissue, so that damage to uninvolved tissue by the neutral electrode 56 is avoided.

By contrast, the neutral electrode 56 is not insulated on its inner face 70 (cf. FIG. 5) directed toward the active electrode 54, with the result that a current flow can be established between the active electrode 54 and the inner face 70 of the neutral electrode 56 when tissue and/or an electrically conductive liquid, for example an irrigation liquid for which an isotonic saline solution is used, is present between the inner face 70 of the neutral electrode 56 and the active electrode 54.

As is indicated by broken lines in FIG. 4, the insulation of the active electrode 54 can extend still farther to the outer end of the active electrode 54, so that a higher current density is obtained at the outer end of the active electrode 54, by which means the cutting action of the active electrode 54 can be further improved at its outer end.

The function of the instrument 12 and of the high-frequency generator 14 will now be described in detail with reference to FIG. 6 and FIG. 1.

The high-frequency generator 14 is able, at least at certain times, to output a power of at least 200 watt.

Figure 6A:
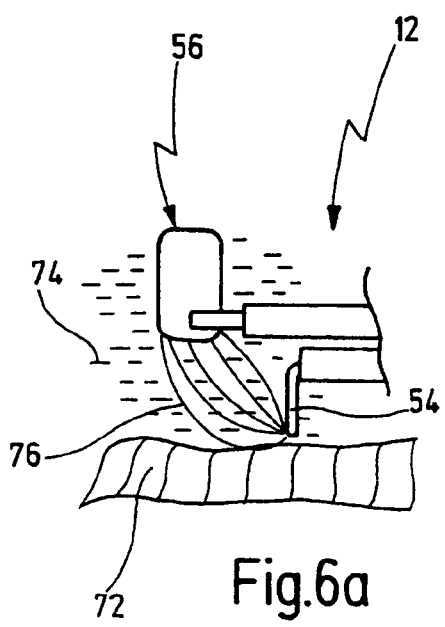
FIGS. 6a) and 6b) show the distal end of the instrument in FIG. 1 on an enlarged scale, FIG. 6a) showing the initial cutting procedure, and FIG. 6b) showing the continued cutting procedure.

In FIG. 6a), reference number 72 designates tissue into which a tissue incision is to be made with the instrument 12. The active electrode 54 and the neutral electrode 56 are here surrounded by an electrically conductive liquid since, in such procedures irrigation is performed with an isotonic saline solution.

Figure 6B:
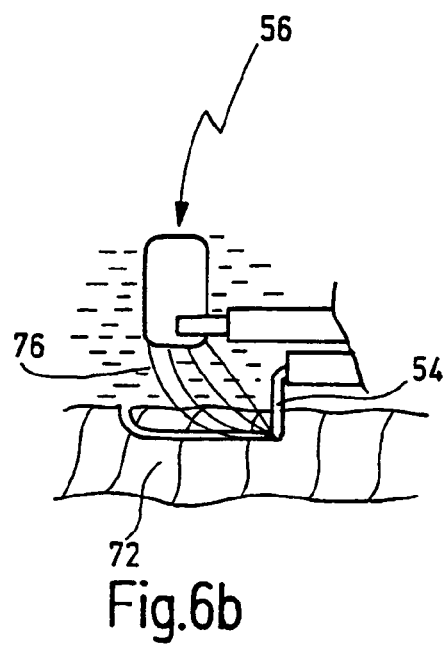

When, as is shown in FIG. 6a), the electrode 54 is placed on the tissue 72 and the high-frequency generator 14 is switched on, the higher impedance of the tissue 72 compared to the liquid 74 means that a current flow is first established between the active electrode 54 and the neutral electrode 56, as is indicated by current lines 76 in FIG. 6a). In this state, the current flow does not pass through the tissue 72, or, if it does, it does so only slightly. In order to ensure, during this initial cutting, that the current flow through the tissue 72 is sufficient for electrical cutting, the power output by the high-frequency generator is now increased temporarily to at least 200 watt, specifically for a duration of approximately 0.2 s (at a frequency of 150-350 kHz). It is now possible for the active electrode 54 to penetrate into the tissue 72 and form an incision therein, as is indicated in FIG. 6b).

By actuating the handle 34, the active electrode 54, and along with it the neutral electrode 56 connected mechanically to it via the electrode carrier 24, is now pulled in the proximal direction in order to cut the tissue 72. In this continued cutting procedure, the power output by the high-frequency generator 14 is again reduced, specifically below 200 watt, in order to avoid carbonization of the tissue 72. An increase in the power output by the high-frequency generator 14 is now no longer necessary because the current flow between the active electrode 54 and the neutral electrode 56 also extends sufficiently through the tissue 72. If, however, during the continued cutting, the current flow between the active electrode 54 and the neutral electrode 56 breaks off, the power output by the high-frequency generator 14 can again be temporarily increased until a current flow is once more present.

What is claimed is:

1. A bipolar medical instrument for cutting tissue under the action of high-frequency current, comprising
    an elongate electrode carrier extending in a longitudinal direction and having a distal end,
    an active electrode arranged at said distal end of said electrode carrier, a neutral electrode arranged at said distal end of said electrode carrier adjacent to said active electrode and arranged entirely to the distal side of said active electrode so as to be spaced apart from said active electrode in said longitudinal direction, said neutral electrode and said active electrode being also spaced apart from one another in a direction transverse to said longitudinal direction, without having a spatial overlap region in said longitudinal direction and said direction transverse to said longitudinal direction,
    wherein said active electrode is configured as a wire loop.

2. The instrument of claim 1, wherein on at least one of said electrode carrier and said neutral electrode, at least one element is present which prevents electrically conductive contact between tissue and an outer face of said neutral electrode directed away from said active electrode, and which, when said neutral electrode changes position, moves along with said neutral electrode.

3. The instrument of claim 2, wherein said at least one element is itself electrically insulating.

4. The instrument of claim 2, wherein said at least one element is made from a material selected from the group consisting of ceramic materials and plastic materials.

5. The instrument of claim 2, wherein said element is formed by a coating of said neutral electrode.

6. The instrument of claim 2, wherein said at least one element is secured directly on said outer face of said neutral electrode directed away from said active electrode.

7. The instrument of claim 2, wherein said at least one element completely covers said outer face of said neutral electrode.

8. The instrument of claim 2, wherein said at least one element prevents electrically conductive contact between at least one of a distal end face and a proximal end face of said neutral electrode and tissue.

9. The instrument of claim 8, wherein said at least one element covers the complete area of said at least one of said distal end face and said proximal end face of said neutral electrode.

10. An electrosurgical system, comprising a high-frequency generator, and comprising a bipolar medical instrument for cutting tissue under the action of high-frequency current, said bipolar medical instrument comprising
an elongate electrode carrier extending in a longitudinal direction and having a distal end,
an active electrode arranged at said distal end of said electrode carrier, a neutral electrode arranged at said distal end of said electrode carrier adjacent to said active electrode and arranged entirely to the distal side of said active electrode so as to be spaced apart from said active electrode in said longitudinal direction, said neutral electrode and said active electrode being also spaced apart from one another in a direction transverse to said longitudinal direction, without having a spatial overlap region in said longitudinal direction and said direction transverse to said longitudinal direction,
said high-frequency generator being connectable with said bipolar medical instrument for supplying a high-frequency voltage between said active electrode and said neutral electrode,
wherein said active electrode is configured as a wire loop.

11. The system of claim 10, wherein said high-frequency generator is able to output power of at least 200 W.

12. The system of claim 10, wherein said high-frequency generator has an output regulator which is such that the power output by said high-frequency generator before and during penetration of said active electrode and/or tissue is greater during continued cutting when said active electrode has penetrated into said tissue.

13. A bipolar medical instrument for cutting tissue under the action of high-frequency current, comprising
an elongate electrode carrier extending in a longitudinal direction and having a distal end,
an active electrode arranged at said distal end of said electrode carrier, a neutral electrode arranged at said distal end of said electrode carrier adjacent to said active electrode and arranged entirely to the distal side of said active electrode so as to be spaced apart from said active electrode in said longitudinal direction, said neutral electrode and said active electrode being also spaced apart from one another in a direction transverse to said longitudinal direction, without having a spatial overlap region in said longitudinal direction and said direction transverse to said longitudinal direction,
wherein said neutral electrode is configured as a tape loop.

14. The instrument of claim 13, wherein said neutral electrode has a curvature oriented away from said active electrode.

15. The instrument of claim 13, wherein on at least one of said electrode carrier and said neutral electrode, at least one element is present which prevents electrically conductive contact between tissue and an outer face of said neutral electrode directed away from said active electrode, and which, when said neutral electrode changes position, moves along with said neutral electrode.

16. The instrument of claim 15, wherein said at least one element is itself electrically insulating.

17. The instrument of claim 15, wherein said at least one element is made from a material selected from the group consisting of ceramic materials and plastic materials.

18. The instrument of claim 15, wherein said element is formed by a coating of said neutral electrode.

19. The instrument of claim 15, wherein said at least one element is secured directly on said outer face of said neutral electrode directed away from said active electrode.

20. The instrument of claim 15, wherein said at least one element completely covers said outer face of said neutral electrode.

21. The instrument of claim 15, wherein said at least one element prevents electrically conductive contact between at least one of a distal end face and a proximal end face of said neutral electrode and tissue.

22. The instrument of claim 21, wherein said at least one element covers the complete area of said at least one of said distal end face and said proximal end face of said neutral electrode.

23. A bipolar medical instrument for cutting tissue under the action of high-frequency current, comprising
an elongate electrode carrier extending in a longitudinal direction and having a distal end,
an active electrode arranged at said distal end of said electrode carrier, a neutral electrode arranged at said distal end of said electrode carrier adjacent to said active electrode and arranged entirely to the distal side of said active electrode so as to be spaced apart from said active electrode in said longitudinal direction, said neutral electrode and said active electrode being also spaced apart from one another in a direction transverse to said longitudinal direction, without having a spatial overlap region in said longitudinal direction and said direction transverse to said longitudinal direction,
wherein on at least one of said electrode carrier and said neutral electrode, at least one element is present which prevents electrically conductive contact between tissue and an outer face of said neutral electrode directed away from said active electrode, and which, when said neutral electrode changes position, moves along with said neutral electrode;
said at least one element being arranged on said outer face of said neutral electrode directed away from said active electrode.

24. The instrument of claim 23, wherein said at least one element is itself electrically insulating.

25. The instrument of claim 23, wherein said at least one element is made from a material selected from the group consisting of ceramic materials and plastic materials.

26. The instrument of claim 23, wherein said element is formed by a coating of said neutral electrode.

27. The instrument of claim 23, wherein said at least one element is secured directly on said outer face of said neutral electrode directed away from said active electrode.

28. The instrument of claim 23, wherein said at least one element completely covers said outer face of said neutral electrode.

29. The instrument of claim 23, wherein said at least one element prevents electrically conductive contact between at least one of a distal end face and a proximal end face of said neutral electrode and tissue.

30. The instrument of claim 29, wherein said at least one element covers the complete area of said at least one of said distal end face and said proximal end face of said neutral electrode.

* * * * *